United States Patent [19]

Takasugi et al.

[11] 4,268,251

[45] May 19, 1981

[54] BORING NEEDLE DEVICE FOR TREATMENT OF A DENTAL ROOT CANAL

[76] Inventors: Mitsuo Takasugi, 74 Kuritaya, Kanagawa-ku, Yokohama, Japan, 221; Yoshio Okuyama, 13-7 Shimouma 3-chome, Setagaya-ku, Tokyo 154, Japan

[21] Appl. No.: 101,862

[22] PCT Filed: Jul. 16, 1979

[86] PCT No.: PCT/JP78/00026

§ 371 Date: Jul. 17, 1979

§ 102(e) Date: Jul. 16, 1979

[87] PCT Pub. No.: WO79/00300

PCT Pub. Date: May 31, 1979

[30] Foreign Application Priority Data

Nov. 17, 1977 [JP] Japan .................................. 52-153480
Sep. 13, 1978 [JP] Japan .................................. 53-113261

[51] Int. Cl.³ .............................................. A61C 5/02
[52] U.S. Cl. ....................................... 433/75; 433/102
[58] Field of Search ............. 433/102, 75; 128/329 A; 30/293, 368

[56] References Cited

U.S. PATENT DOCUMENTS

| | | | |
|---|---|---|---|
| 3,562,913 | 2/1971 | Saffro | 433/75 |
| 3,713,221 | 1/1973 | Malmin | 433/75 |
| 3,905,375 | 9/1975 | Toyama | 128/329 A |
| 3,924,334 | 12/1975 | Lentine et al. | 433/102 |
| 4,165,562 | 8/1979 | Sarfatti | 433/75 |

FOREIGN PATENT DOCUMENTS 2531482 2/1976 Fed. Rep. of Germany ...... 433/102

*Primary Examiner*—Gene Mancene
*Assistant Examiner*—John J. Wilson
*Attorney, Agent, or Firm*—George B. Oujevolk

[57] ABSTRACT

A boring needle device for treatment of a dental root canal has a boring needle useful upon treating a dental root canal. The needle can be adjusted, without resort to any special adjustment expedient, to a boring effective needle length which is corresponding to a depth of the canal preliminarily determined by separate means. The needle is secured at the proximal end to a grip member which is caused to stepwisely minutely slide relative to a sleeve member whereby a length of the needle projecting from the sleeve member can be finely adjusted by a determined minute distance.

8 Claims, 4 Drawing Figures

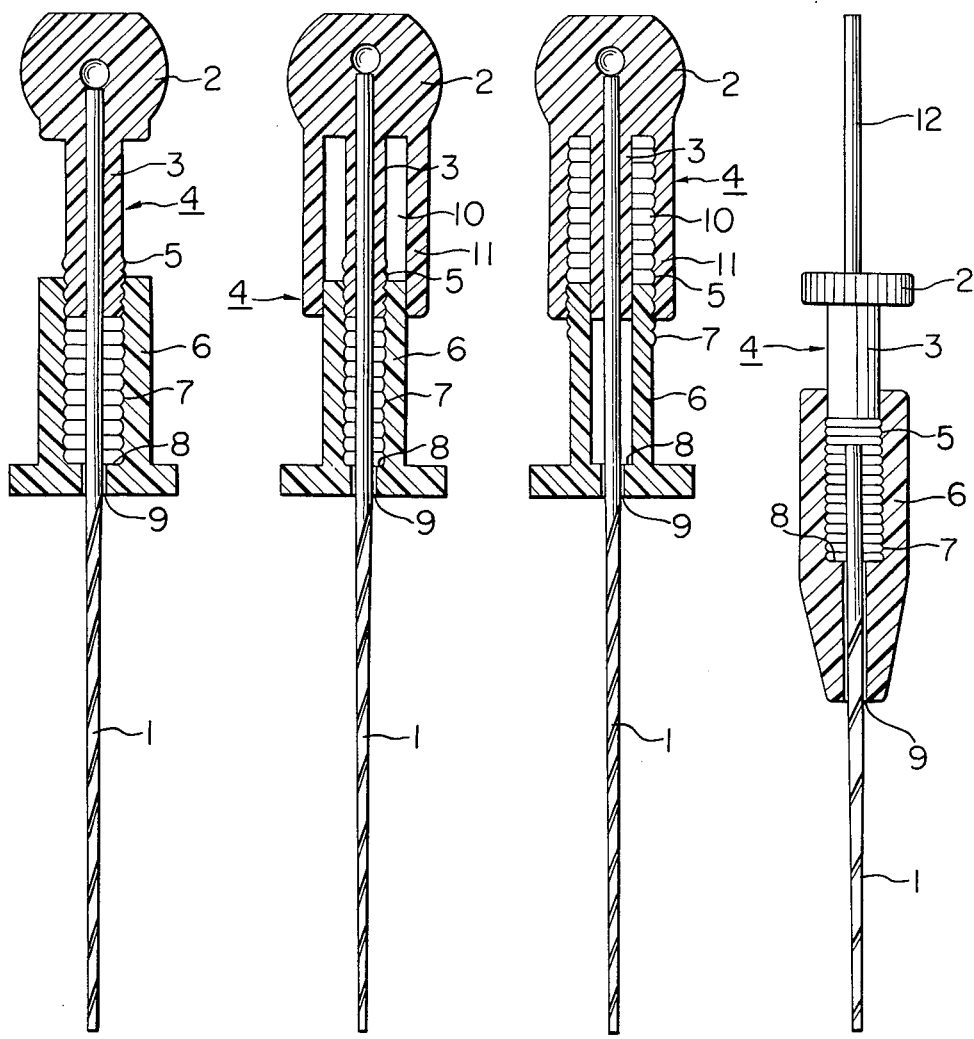

4,268,251

BORING NEEDLE DEVICE FOR TREATMENT OF A DENTAL ROOT CANAL

FIELD OF THE INVENTION

This invention relates to a boring needle device for treatment of a dental root canal, whose boring needle useful upon treating a dental root canal can be adjusted, without resort to any special adjustment expedient, to a boring or drilling effective needle length which is corresponding to a depth of the canal preliminarily determined by means of an X-ray photographer or a probe for root canals.

BACKGROUNDS OF THE INVENTION

Boring needle devices of the type above mentioned are known which have effective needle length adjustable without use of any adjustment expedient, and one example thereof is provided with an annular member of an elastomeric material, such as rubber, etc., having its center aperture through which extends the needle and thus fitted on the needle snugly by action of elasticity of the material to be shiftable for adjustment of an effective needle length. The other example has double nuts meshingly fitted on the needle, with thread being formed thereon, to be displaced for adjustment of an effective needle length. In the first mode, the annular member is subject to flexure deformation by contours of the top faces of teeth, or to rotational friction generated by the tooth top faces with which the annular member is abuttingly in contact, so that the needle is differentially turned in the center aperture of the annular member, with the annular member being lifted along the needle. The mode has the disadvantage that an effective needle length once defined by position of the annular member is likely to inadvertently vary, lacking satisfactory preciseness. The second mode above is disadvantageous in involving burdensome, awkward manipulation of positioning the double nuts to adjust an effective needle length. An example of such dental needle devices which have effective needle length variable with use of an adjustment expedient is described in Japanese patent No. 882,362 as published under 52-9,950. It is obviously cumbersome to set such an adjustment device on the needle device as inherently required in this type of mode to establish an intended effective needle length by the aid of a further additional utensil, which attachments may restrict an oral space available for surgical treatment. A needle device has been demanded which is handy and easily manipulable and dissolves the above stated problems encountered in operationality with any known devices.

SUMMARY OF THE INVENTION

According to the invention, there is provided a boring needle device for treatment of a root canal comprises a grip member formed by a head portion and a shaft portion depending from the head portion, a needle, such as reamer, file or the like, having its proximal end coaxially embedded and secured in the shaft portion of the grip member, and a sleeve member having a guide bore through which the needle extends and closely fitted with the grip member in an elastic frictional relationship therewith, the fitting circumferential surfaces of the grip and the sleeve members having a plurality of annular grooves and ridges formed thereon to be spaced from each other at a determined distance, thus providing means permitting said sleeve to stepwisely minutely slide relative to the grip member by action of force exerted in an axial direction and to be self-retained in the grip member at a determined adjusted position. In the arrangement stated, a length of the needle projecting from the sleeve member is enabled to be adjusted correspondingly to a distance of the depth of a root canal and be self-fixed in an adjusted position, thus facilitating adjustment and establishment of an effective needle length.

BRIEF DESCRIPTION OF THE ACCOMPANYING DRAWINGS

FIG. 1 shows a longitudinally sectional view of one embodiment of the invention;

FIG. 2 similarly shows another embodiment of the invention;

FIG. 3 similarly shows still another embodiment of the invention; and

FIG. 4 also similarly shows a further embodiment of the invention.

BEST MODES OF THE INVENTION

Embodiments of the invention will be described in reference to the accompanying drawings.

An embodiment shown in FIG. 1 has a grip member 4 having a head portion 2 and a shaft portion 3 of rigid synthetic resin centrally depending from the head portion, and a needle 1 having its proximal end portion coaxially embedded in the shaft portion 3. The shaft portion 3 has a plurality of annular ridges 5 formed in the circumferential surface adjacent the distal end thereof to be spaced from each other at a determined distance, say, at a distance of 0.5 mm. A sleeve member 6 of elastic synthetic resin is fitted on the shaft portion 3 of the grip member. The sleeve member 6 has a plurality of annular grooves 7 formed entirely in the inner circumferential surface thereof to be closely engaged in complementary relation with the ridges 5 on the shaft portion 3, and a bottom portion 8 in which formed is a guide aperture through which the needle is extending.

In use, the grip member 4 is manipulated to forceslide relative to the sleeve member 6 receiving its shaft portion 3, with the needle extending through aperture 9 in the bottom 8, to cause the annular ridges 5 in the shaft portion 3 to stepwisely shift in the engaging position with annular grooves 7 in the sleeve member 6 by the aid of elasticity of the sleeve member 6, allowing both members to slide relative to each other at a rate of the above mentioned minutely determined distance, varying their total length. This permits a length of the needle 1 projecting from the sleeve member 6 to be adjusted by a unit of the small space of the individual distance between the grooves. In other words, manipulation of the shaft portion 3 of grip member 4 to slide in the sleeve member 6 enables a projecting length of needle 1 to vary to a corresponding distance to a depth of a dental root canal to be treated.

Another embodiment of the invention is shown in FIG. 2 and is similar to the mode above stated, except that the grip member 4 has an outer sleeve portion 11 integrally formed about the shaft portion 3 to be spaced therefrom by an annular spacing 10 of a corresponding distance to a wall thickness of the sleeve member 6. A similar manipulative action may be performed as in the first embodiment, with the sleeve member 6 being received in the spacing 10 between the shaft and the outer sleeve portions 3 and 11 of the grip member 4, to vary an overlapping distance of the fitted grip and sleeve members 4 and 6 and accordingly a length of the needle projecting from the sleeve member 6.

Still another embodiment shown in FIG. 3 is similar to that of FIG. 2, except that the ridge/groove means 5 and 7 are not formed in the circumferential surface of shaft portion 3 and in the inner circumferential surface of the sleeve member 6, but in the inner circumferential surface of the outer sleeve portion 11 of the grip member 4 and in the circumferential surface of the sleeve member 6 to be closely fitted with each other. A similar manipulative action may be made to adjust a projecting length of the needle.

A further embodiment is shown in FIG. 4 which is similar to the first embodiment, except that the sleeve member 6 is tapered toward the lower end to have a distal end face which is adapted to abut against an appropriate location of a tooth for facilitating boring operation of the root canal.

In each of the embodiments, a chuck grip stem 12 may be provided in the grip member 4 to extend in the opposite direction to the boring needle, for coupling with a power driven or manual chuck for driving the needle.

Once a length of the needle projecting from the sleeve member 6 has been adjusted to a corresponding length to a measured depth of the root canal of a tooth to be treated, the needle device is manipulated with the head portion being thumbed by a dentist to perform a drilling or boring operation until the lower end face of the sleeve member 6 reaches the top face of the tooth, which precisely indicates that the distal end of the needle has reached the predetermined distance of depth to enable the dentist to fully perform an intended operation.

The grip and the sleeve members 4 and 6 are elastically fitted on circumferential surfaces in which a plurality of ridges 5 and grooves 7 are formed respectively to be spaced at a predetermined very small distance, permitting the grip member 4 and the sleeve member 6 to be fitted for stepwise sliding under manually exerted force and be frictionally self-retained relatively at any adjusted position. A projecting length of the needle can be thus easily finely adjusted to a corresponding position to a depth of the dental root canal, without any special operator's skill being called for.

We claim:

1. A boring needle device for treatment of a dental root canal, comprising a grip member (4) having a head portion (2) and a shaft portion (3) centrally depending from said head portion, a needle (1) having its proximal end coaxially embedded and secured in said shaft portion, and a sleeve member (6) closely fitted on said grip member (4) in an elastic relationship therewith, the fitting surfaces of said grip and said sleeve members (4) and (6) having a plurality of axially spaced annular grooves and ridges (5), (7) formed thereon spaced from each other at a determined distance, thus providing means permitting said grip member (4) to closely slide relative to said sleeve portion (6) stepwisely by a minute amount and be self-retained in one of a plurality of desired positions defined by respective ones of said grooves and ridges formed on said sleeve member.

2. A boring needle device according to claim 1, wherein said shaft portion of said grip member has said axially spaced annular grooves and ridges formed on an exterior circumferential surface thereof, and wherein said sleeve member encompasses at least a portion of said shaft portion and has said axially spaced annular grooves and ridges formed on an interior circumferential surface thereof.

3. A boring needle device according to claim 1, wherein said shaft portion of said grip member has said axially spaced annular grooves and ridges formed on an exterior circumferential surface thereof, wherein said sleeve member encompasses at least a portion of said shaft portion and has said axially spaced annular grooves and ridges formed on an interior circumferential surface thereof, wherein said grip member further comprises an outer sleeve portion spaced from said shaft portion by an annular spacing, and wherein an upper portion of said sleeve member extends into said annular spacing between said outer sleeve portion and said shaft portion.

4. A boring needle device according to claim 3, wherein said sleeve member has a wall thickness substantially equal to said annular spacing.

5. A boring needle device according to claim 1, wherein said grip member further comprises an outer sleeve portion spaced from said shaft portion by an annular spacing substantially equal to the wall thickness of said sleeve member, said fitting surfaces having annular grooves and ridges being formed on an interior circumferential surface of said outer sleeve portion and an exterior circumferential surface of said sleeve member.

6. A boring needle device according to claim 5, wherein confronting surfaces of said portion and said sleeve member are substantially smooth.

7. A boring needle device according to claim 1, 2, 3, 4, 5, or 6, wherein said sleeve member has a lower surface contactable by a surface of a tooth to limit the depth of pentration of the boring needle device into a dental root canal.

8. A boring needle device according to claim 7, wherein said sleeve member is tapered towards its lower surface to facilitate a boring operation.

* * * * *